United States Patent
Wang et al.

(10) Patent No.: US 9,034,904 B2
(45) Date of Patent: May 19, 2015

(54) FORMS OF DEXLANSOPRAZOLE AND PROCESSES FOR THE PREPARATION THEREOF

(75) Inventors: Fan Wang, Hamilton (CA); Kevin W. Kells, Cambridge (CA); Kaarina Milnes, London (CA); Cameron L. McPhail, Brantford (CA)

(73) Assignee: APOTEX PHARMACHEM INC., Brantford (CA)

( * ) Notice: Subject to any disclaimer, the term of this patent is extended or adjusted under 35 U.S.C. 154(b) by 292 days.

(21) Appl. No.: 13/391,327

(22) PCT Filed: Aug. 19, 2010

(86) PCT No.: PCT/CA2010/001276
§ 371 (c)(1),
(2), (4) Date: Nov. 13, 2012

(87) PCT Pub. No.: WO2011/020189
PCT Pub. Date: Feb. 24, 2011

(65) Prior Publication Data
US 2013/0065927 A1  Mar. 14, 2013

Related U.S. Application Data

(60) Provisional application No. 61/235,205, filed on Aug. 19, 2009, provisional application No. 61/243,359, filed on Sep. 17, 2009.

(51) Int. Cl.
*A61K 31/44* (2006.01)
*C07D 401/12* (2006.01)
*A61K 31/4439* (2006.01)
*C07D 235/28* (2006.01)

(52) U.S. Cl.
CPC ............ *C07D 401/12* (2013.01); *C07D 235/28* (2013.01); *A61K 31/4439* (2013.01)

(58) Field of Classification Search
CPC .......................... A61K 31/4439; C07D 235/28
USPC ........................................................ 514/341
See application file for complete search history.

(56) References Cited

U.S. PATENT DOCUMENTS

2008/0177087 A1 *  7/2008  Murthy et al. ................. 548/537

FOREIGN PATENT DOCUMENTS

CA        2738458      *  7/2009
WO   WO 2010/039885 A2  *  4/2010

* cited by examiner

*Primary Examiner* — James D Anderson
*Assistant Examiner* — Meghan Finn

(57) ABSTRACT

Provided is dexlansoprazole propylene glycolate hydrate. Polymorphic forms thereof are also provided. The dexlansoprazole propylene glycolate hydrate maybe such that the propylene glycol component is present in approximately equal proportions of (R) absolute configuration and (S) absolute configuration, or present in predominantly (R) absolute configuration, or predominantly (S) absolute configuration. Salts of dexlansoprazole are also provided. In particular, crystalline dexlansoprazole isopropylammonium salt and crystalline MTBE solvate of dexlansoprazole t-butylammonium salt are provided. Pharmaceutical formulations comprising dexlansoprazole propylene glycolate hydrate are also provided. Furthermore, processes for preparation of dexlansoprazole propylene glycolate hydrate are provided.

16 Claims, 9 Drawing Sheets

FORMS OF DEXLANSOPRAZOLE AND PROCESSES FOR THE PREPARATION THEREOF

TECHNICAL FIELD

The present invention relates to polymorphic and salt forms of dexlansoprazole.

BACKGROUND

Dexlansoprazole 1, is chemically known as (R)-2-[[[3-methyl-4-(2,2,2-trifluoroethoxy)-2-pyridinyl]methyl]sulfinyl]-1H-benzimidazole, and is the (R)-enantiomer of the proton pump inhibitor lansoprazole. It is currently marketed as KAPIDEX®.

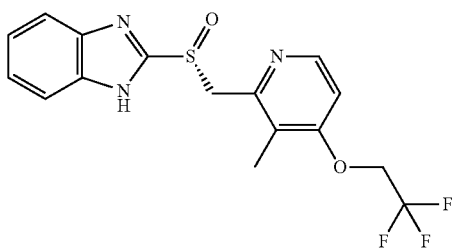

Dexlansoprazole and lansoprazole have activity such as gastric acid secretion suppressing effect and gastric mucosa defensive effect. Both are useful as antiulcer agents and are applied in the treatment and maintenance of patients with erosive oesophagitis and non-erosive reflux disease, i.e. gastro-oesophageal reflux disease (GERD or GORD).

U.S. Pat. No. 6,462,058 discloses a novel crystal of (R)-2-[[[3-methyl-4-(2,2,2-trifluoroethoxy)-2-pyridinyl]methyl]sulfinyl]-1H-benzimidazole or a salt thereof useful for an excellent antiulcer agent.

U.S. Pat. No. 7,169,799 relates to a production method of a crystal of (R)-2-[[[3-methyl-4-(2,2,2-trifluoroethoxy)-2-pyridyl]methyl]sulfinyl]benzimidazole.n'H$_2$O (wherein n' is about 0 to about 0.1) or a salt thereof, which characteristically includes crystallization from an organic solvent solution or suspension in which (R)-2-[[[3-methyl-4-(2,2,2-trifluoroethoxy)-2-pyridyl]methyl]sulfinyl]-benzimidazole.nH$_2$O (wherein n is about 0.1 to about 1.0) or a salt thereof has been dissolved or suspended, and the like, and provides a convenient method for efficiently producing an optically active sulfoxide derivative having an extremely high enantiomer excess in high yield at an industrial large scale.

U.S. Pat. No. 7,271,182 discloses a sodium salt, magnesium salt, lithium salt, potassium salt, calcium salt or barium salt of (R)-2-[[[3-methyl-4-(2,2,2-trifluoroethoxy)-2-pyridinyl]methyl]sulfinyl]-1H-benzimidazole, and a pharmaceutical composition comprising the salt. The novel salt is useful as an excellent antiulcer agent.

U.S. Pat. No. 7,285,668 relates to a production method of a crystal of (R)-lansoprazole or (S)-lansoprazole, which includes crystallization at a temperature of about 0° C. to about 35° C. from a C$_{1-4}$ alkyl acetate solution containing (R)-lansoprazole or (S)-lansoprazole at a concentration of about 0.1 g/mL to about 0.5 g/mL and the like. According to the production method of the invention, a crystal of (R)-lansoprazole or (S)-lansoprazole superior in preservation stability can be produced efficiently on an industrial scale.

WO 2005011692 relates to alkaline salts of proton pump inhibitors and to medicaments comprising these compounds.

CA 2502219 provides a process for producing unstable amorphous benzimidazole compounds having a proton pump inhibitor function, and stable solid preparations for medicinal use containing these compounds which are produced by blending such an amorphous benzimidazole compound with a non-toxic base, such as a basic inorganic salt, forming an intermediate coating layer on the layer containing the active ingredient and further forming an enteric coating layer or a release-controlling coating layer.

SUMMARY

The present invention relates to a crystalline propylene glycolate hydrate of dexlansoprazole. The present invention further relates to dexlansoprazole isopropylammonium salt and the methyl tert-butyl ether (MTBE) solvate of dexlansoprazole t-butylammonium salt.

As used herein, the term "propylene glycolate hydrate" is synonymous with the term "propylene glycol hydrate" as used in U.S. provisional patent 61/235,205, filed Aug. 19, 2009.

Dexlansoprazole propylene glycolate hydrate of the present invention exhibits a number of unexpected properties. Dexlansoprazole propylene glycolate hydrate of the present invention shows increased chemical stability compared to other known forms of dexlansoprazole such as the amorphous form. Additionally, the solubility properties of dexlansoprazole propylene glycolate hydrate enable efficient purification from difficult to remove impurities including stereoisomeric impurities such as the (S)-isomer of lansoprazole and chemical impurities such as the sulfone.

In one embodiment, the present invention relates to dexlansoprazole propylene glycolate monohydrate. Dexlansoprazole forms a crystalline solvate monohydrate with propylene glycol wherein the molar ratio of dexlansoprazole to propylene glycol to water is approximately 1:1:1.

Propylene glycol contains an asymmetrical carbon atom and so exists in two enantiomeric forms, the (R)-isomer and the (S)-isomer. In an embodiment, the mainly optically pure (R)-isomer or the mainly optically pure (S)-isomer of propylene glycol may be used to enrich the stereochemical purity of dexlansoprazole by preferential formation of a solvate containing one of the enantiomeric forms of propylene glycol. In another embodiment, a racemic mixture of propylene glycol may also be used to enrich the stereochemical purity of dexlansoprazole.

In one embodiment, the present invention relates to Form APO-I of dexlansoprazole propylene glycolate hydrate, which exhibits increased chemical stability compared to other known forms of dexlansoprazole, such as the amorphous form. For example, the chemical purity by High-performance liquid chromatography (HPLC) (area %) of Form APO-I dexlansoprazole propylene glycolate hydrate is essentially unchanged following 1 week of storage at 40° C. and 75% relative humidity (40° C./75% RH), whereas the amorphous form shows a reduction in chemical purity of 8.5 area % under the same storage conditions.

In another embodiment, the present invention relates to Form APO-II of dexlansoprazole propylene glycolate hydrate. Form APO-II also exhibits improved chemical stability compared to other known forms of dexlansoprazole such as the amorphous form.

In one embodiment, the present invention relates to dexlansoprazole isopropylammonium salt. Dexlansoprazole reacts with isopropylamine to form a crystalline isopropylammonium salt wherein the molar ratio of dexlansoprazole to isopropylamine is approximately 1:1.

In another embodiment, the present invention relates to an MTBE solvate of dexlansoprazole t-butylammonium salt. Dexlansoprazole reacts with t-butyl amine in the presence of MTBE to form a crystalline MTBE solvate of the t-butylammonium salt wherein the molar ratio of dexlansoprazole to t-butyl amine to MTBE is approximately 3:3:2.

The amine salts of the present invention may offer several advantages. For example, the salts of the present invention may be easily isolated and conveniently handled due to their crystalline nature. The solubility properties of the amine salts of the present invention may enable them to be easily and efficiently purified from related stereoisomeric and chemical impurities. The salts of the present invention may exhibit good chemical and polymorphic stability. In some embodiments, the alkylammonium salts of the present invention may be particularly useful as intermediates for purification and enrichment of enantiopurity in the synthesis of dexlansoprazole or salts thereof.

In illustrative embodiments of the present invention, there is provided dexlansoprazole propylene glycolate hydrate.

In illustrative embodiments of the present invention, there is provided dexlansoprazole propylene glycolate hydrate described herein wherein the propylene glycol component is present in approximately equal proportions of (R) absolute configuration and (S) absolute configuration.

In illustrative embodiments of the present invention, there is provided dexlansoprazole propylene glycolate hydrate described herein wherein the propylene glycol component is present in predominantly (R) absolute configuration.

In illustrative embodiments of the present invention, there is provided dexlansoprazole propylene glycolate hydrate described herein wherein the propylene glycol component is present in predominantly (S) absolute configuration.

In illustrative embodiments of the present invention, there is provided dexlansoprazole propylene glycolate hydrate described herein wherein the propylene glycol component is present in an (R):(S) ratio of any proportion of (R) absolute configuration of propylene glycol and (S) absolute configuration of propylene glycol provided that the (R):(S) ratio is not approximately 1:1.

In illustrative embodiments of the present invention, there is provided a pharmaceutical formulation comprising dexlansoprazole propylene glycolate hydrate described herein and a pharmaceutically acceptable excipient.

In illustrative embodiments of the present invention, there is provided Form APO-I dexlansoprazole propylene glycolate hydrate.

In illustrative embodiments of the present invention, there is provided Form APO-I dexlansoprazole propylene glycolate hydrate described herein having a PXRD diffractogram comprising peaks, in terms of degrees 2θ, at approximately 5.6, 7.6, 9.8, 11.3, 17.0, 18.2 and 28.4.

In illustrative embodiments of the present invention, there is provided Form APO-I dexlansoprazole propylene glycolate hydrate described herein having a PXRD diffractogram comprising peaks, in terms of degrees 2θ, at approximately 5.6, 7.6, 9.8, 11.3, 17.0, 18.2, 19.7, 20.3, 22.6, 27.6 and 28.4.

In illustrative embodiments of the present invention, there is provided Form APO-I dexlansoprazole propylene glycolate hydrate described herein having a PXRD diffractogram substantially similar to the PXRD diffractogram as depicted in FIG. 1.

In illustrative embodiments of the present invention, there is provided Form APO-I dexlansoprazole propylene glycolate hydrate described herein having a PXRD diffractogram as depicted in FIG. 1.

In illustrative embodiments of the present invention, there is provided Form APO-I dexlansoprazole propylene glycolate hydrate described herein having a PXRD diffractogram substantially similar to the PXRD diffractogram as depicted in FIG. 6.

In illustrative embodiments of the present invention, there is provided Form APO-I dexlansoprazole propylene glycolate hydrate described herein having a PXRD diffractogram as depicted in FIG. 6.

In illustrative embodiments of the present invention, there is provided Form APO-I dexlansoprazole propylene glycolate hydrate described herein having a 1% KBr FTIR spectrum comprising peaks, in terms of $cm^{-1}$, at approximately 3328, 3025, 2963, 2893, 2816, 1620, 1320 and 1292.

In illustrative embodiments of the present invention, there is provided Form APO-I dexlansoprazole propylene glycolate hydrate described herein having a 1% KBr FTIR spectrum comprising peaks, in terms of $cm^{-1}$, at approximately 3328, 3025, 2963, 2893, 2816, 1620, 1584, 1478, 1444, 1320, 1292, and 1266.

In illustrative embodiments of the present invention, there is provided Form APO-I dexlansoprazole propylene glycolate hydrate described herein having a FTIR spectrum substantially similar to the FTIR spectrum as depicted in FIG. 2.

In illustrative embodiments of the present invention, there is provided Form APO-I dexlansoprazole propylene glycolate hydrate described herein having a FTIR spectrum as depicted in FIG. 2.

In illustrative embodiments of the present invention, there is provided Form APO-I dexlansoprazole propylene glycolate hydrate described herein having a DSC thermogram comprising an endothermic peak with a peak onset temperature of approximately 75° C. and a peak maximum of approximately 77° C.

In illustrative embodiments of the present invention, there is provided Form APO-I dexlansoprazole propylene glycolate hydrate described herein having a DSC thermogram substantially similar to the DSC thermogram as depicted in FIG. 3.

In illustrative embodiments of the present invention, there is provided Form APO-I dexlansoprazole propylene glycolate hydrate described herein having a DSC thermogram as depicted in FIG. 3.

In illustrative embodiments of the present invention, there is provided Form APO-I dexlansoprazole propylene glycolate hydrate described herein having a DSC thermogram comprising an endothermic peak with a peak onset temperature of approximately 53° C. and a peak maximum of approximately 68° C.

In illustrative embodiments of the present invention, there is provided Form APO-I dexlansoprazole propylene glycolate hydrate described herein having a DSC thermogram substantially similar to the DSC thermogram as depicted in FIG. 9.

In illustrative embodiments of the present invention, there is provided Form APO-I dexlansoprazole propylene glycolate hydrate described herein having a DSC thermogram as depicted in FIG. 9.

In illustrative embodiments of the present invention, there is provided Form APO-I dexlansoprazole propylene glycolate hydrate described herein wherein the propylene glycol component is present in approximately equal proportions of (R) absolute configuration and (S) absolute configuration.

In illustrative embodiments of the present invention, there is provided Form APO-I dexlansoprazole propylene glycolate hydrate described herein wherein the propylene glycol component is present in predominantly (R) absolute configuration.

In illustrative embodiments of the present invention, there is provided Form APO-I dexlansoprazole propylene glycolate hydrate described herein wherein the propylene glycol component is present in predominantly (S) absolute configuration.

In illustrative embodiments of the present invention, there is provided Form APO-I dexlansoprazole propylene glycolate hydrate described herein wherein the propylene glycol component is present in an (R):(S) ratio of any proportion of (R) absolute configuration of propylene glycol and (S) absolute configuration of propylene glycol provided that the (R):(S) ratio is not approximately 1:1.

In illustrative embodiments of the present invention, there is provided a pharmaceutical formulation comprising Form APO-I dexlansoprazole propylene glycolate hydrate described herein and a pharmaceutically acceptable excipient.

In illustrative embodiments of the present invention, there is provided Form APO-II dexlansoprazole propylene glycolate hydrate.

In illustrative embodiments of the present invention, there is provided Form APO-II dexlansoprazole propylene glycolate hydrate described herein having a PXRD diffractogram comprising peaks, in terms of degrees 2θ, at approximately 5.5, 7.0, 10.5, 16.6, 17.9, 19.0, and 26.0.

In illustrative embodiments of the present invention, there is provided Form APO-II dexlansoprazole propylene glycolate hydrate described herein having a PXRD diffractogram comprising peaks, in terms of degrees 2θ, at approximately 5.5, 7.0, 10.5, 13.2, 16.6, 17.9, 19.0, 19.7, 21.3, 22.5 and 26.0.

In illustrative embodiments of the present invention, there is provided Form APO-II dexlansoprazole propylene glycolate hydrate described herein having a PXRD diffractogram substantially similar to the PXRD diffractogram as depicted in FIG. 7.

In illustrative embodiments of the present invention, there is provided Form APO-II dexlansoprazole propylene glycolate hydrate described herein having a PXRD diffractogram as depicted in FIG. 7.

In illustrative embodiments of the present invention, there is provided Form APO-II dexlansoprazole propylene glycolate hydrate described herein having a DSC thermogram comprising an endothermic peak with a peak onset temperature of approximately 78° C. and a peak maximum of approximately 81° C.

In illustrative embodiments of the present invention, there is provided Form APO-II dexlansoprazole propylene glycolate hydrate described herein having a DSC thermogram substantially similar to the DSC thermogram as depicted in FIG. 8.

In illustrative embodiments of the present invention, there is provided Form APO-II dexlansoprazole propylene glycolate hydrate described herein having a DSC thermogram as depicted in FIG. 8.

In illustrative embodiments of the present invention, there is provided Form APO-II dexlansoprazole propylene glycolate hydrate described herein wherein the propylene glycol component is present in approximately equal proportions of (R) absolute configuration and (S) absolute configuration.

In illustrative embodiments of the present invention, there is provided Form APO-II dexlansoprazole propylene glycolate hydrate described herein wherein the propylene glycol component is present in predominantly (R) absolute configuration.

In illustrative embodiments of the present invention, there is provided Form APO-II dexlansoprazole propylene glycolate hydrate described herein wherein the propylene glycol component is present in predominantly (S) absolute configuration.

In illustrative embodiments of the present invention, there is provided Form APO-II dexlansoprazole propylene glycolate hydrate described herein wherein the propylene glycol component is present in an (R):(S) ratio of any proportion of (R) absolute configuration of propylene glycol and (S) absolute configuration of propylene glycol provided that the (R):(S) ratio is not approximately 1:1.

In illustrative embodiments of the present invention, there is provided a pharmaceutical formulation comprising Form APO-II dexlansoprazole propylene glycolate hydrate described herein and a pharmaceutically acceptable excipient.

In illustrative embodiments of the present invention, there is provided a process for preparation of dexlansoprazole propylene glycolate hydrate comprising: a. combining dexlansoprazole with propylene glycol and water in the presence of a first organic solvent to form a mixture; b. heating the mixture to form a solution; c. promoting crystal growth thereby forming crystals; and d. collecting crystals.

In illustrative embodiments of the present invention, there is provided the process for preparation of dexlansoprazole propylene glycolate hydrate described herein wherein the first organic solvent is selected from the group consisting of methyl-tert-butyl-ether, toluene and ethyl acetate.

In illustrative embodiments of the present invention, there is provided the process for preparation of dexlansoprazole propylene glycolate hydrate described herein wherein a volume ratio of amounts of dexlansoprazole:propylene glycol: first organic solvent:water is 1:between from about 0.2 volumes to about 4 volumes:between from about 4 volumes to about 40 volumes:between from about 0.05 volumes to about 2 volumes.

In illustrative embodiments of the present invention, there is provided dexlansoprazole propylene glycolate hydrate prepared by a process described herein.

In illustrative embodiments of the present invention, there is provided crystalline dexlansoprazole isopropylammonium salt.

In illustrative embodiments of the present invention, there is provided crystalline dexlansoprazole isopropylammonium salt described herein having a PXRD diffractogram comprising peaks, in terms of degrees 2θ, at approximately 6.1, 15.2, 16.1, 16.6, 17.5, 17.8, 21.3, 21.8, 22.3, 24.2 and 25.9.

In illustrative embodiments of the present invention, there is provided crystalline dexlansoprazole isopropylammonium salt described herein having a PXRD diffractogram comprising peaks, in terms of degrees 2θ, at approximately 6.1, 8.5, 10.9, 13.9, 15.2, 16.1, 16.6, 17.5, 17.8, 18.7, 19.1, 21.3, 21.8, 22.3, 23.9, 24.2, 25.2, 25.9 and 28.4.

In illustrative embodiments of the present invention, there is provided crystalline dexlansoprazole isopropylammonium salt described herein having a PXRD diffractogram substantially similar to the PXRD diffractogram as depicted in FIG. 4.

In illustrative embodiments of the present invention, there is provided crystalline dexlansoprazole isopropylammonium salt described herein having a PXRD diffractogram as depicted in FIG. 4.

In illustrative embodiments of the present invention, there is provided a pharmaceutical formulation comprising crystalline dexlansoprazole isopropylammonium salt described herein and a pharmaceutically acceptable excipient.

In illustrative embodiments of the present invention, there is provided crystalline MTBE solvate of dexlansoprazole t-butylammonium salt.

In illustrative embodiments of the present invention, there is provided crystalline MTBE solvate of dexlansoprazole t-butylammonium salt described herein having a PXRD diffractogram comprising peaks, in terms of degrees 2θ, at approximately 5.8, 6.8, 8.0, 11.6, 17.3, 19.8, 20.1, 22.8, 24.2 and 24.7.

In illustrative embodiments of the present invention, there is provided crystalline MTBE solvate of dexlansoprazole t-butylammonium salt described herein having a PXRD diffractogram comprising peaks, in terms of degrees 2θ, at approximately 5.8, 6.8, 8.0, 11.6, 13.8, 16.6, 17.3, 19.8, 20.1, 22.8, 24.2 and 24.7.

In illustrative embodiments of the present invention, there is provided crystalline MTBE solvate of dexlansoprazole t-butylammonium salt described herein having a PXRD diffractogram substantially similar to the PXRD diffractogram as depicted in FIG. 5.

In illustrative embodiments of the present invention, there is provided crystalline MTBE solvate of dexlansoprazole t-butylammonium salt described herein having a PXRD diffractogram as depicted in FIG. 5.

In illustrative embodiments of the present invention, there is provided a pharmaceutical formulation comprising crystalline MTBE solvate of dexlansoprazole t-butylammonium salt described herein and a pharmaceutically acceptable excipient.

Other aspects and features of the present invention will become apparent to those ordinarily skilled in the art upon review of the following description of specific embodiments of the invention in conjunction with the accompanying figures.

BRIEF DESCRIPTION OF THE DRAWINGS

In drawings which illustrate embodiments of the invention.

DETAILED DESCRIPTION

Figure 1:
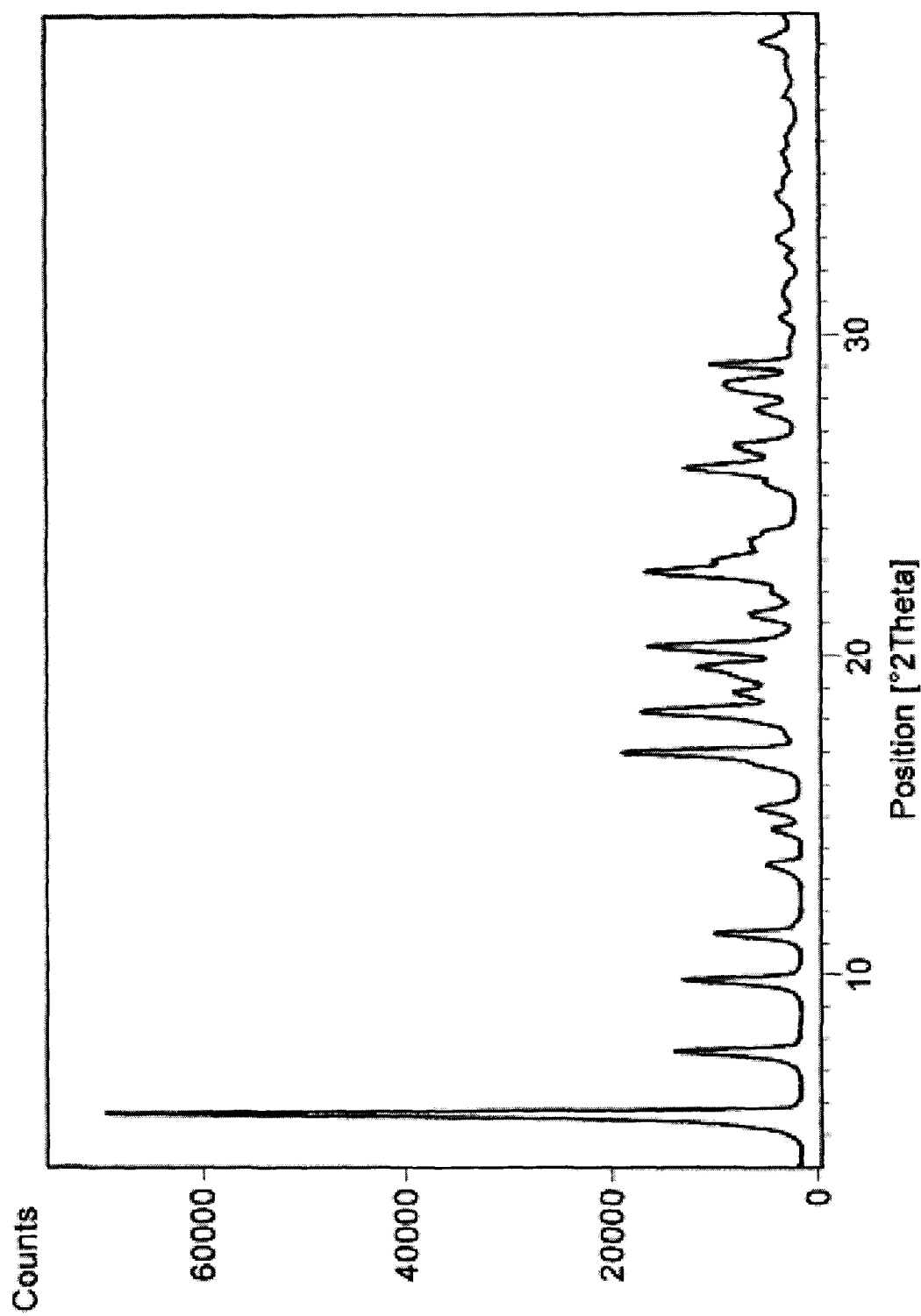
FIG. 1 is a Powder X-Ray Diffraction (PXRD) diffractogram of Form APO-I dexlansoprazole propylene glycolate hydrate after it has been lightly ground (CuKα).

When used in reference to a spectrum and/or data presented in a graph, the term "substantially" should be interpreted as encompassing a diffractogram within acceptable boundaries of experimentation.

When used in reference to a peak in the PXRD diffractogram, the term "approximately" generally means that the peak is within +/−0.2 degrees 2θ of the quoted value.

When used in reference to a peak in the FTIR spectrum, the term "approximately" generally means that the peak is within +/−5 cm$^{-1}$ of the quoted value.

When used in reference to a peak in the DSC thermogram, the term "approximately" generally means that the peak is within +/−1 degrees of the quoted value.

As used herein when referring to a spectrum and/or to data presented in a graph, the term "peak" refers to a feature that one skilled in the art would recognize as not attributable to background noise.

Depending on the nature of the methodology applied and the scale selected to display results obtained from X-ray diffraction analysis, the peak intensities of peaks obtained may vary quite dramatically. For example, it is possible to obtain a relative peak intensity of 0.00% when analyzing one sample of a substance, but another sample of the same substance may show a much different relative intensity for a peak at the same position. This may be due, in part, to the preferred orientation of the sample and its deviation from the ideal random sample orientation, sample preparation and the methodology applied The present invention encompasses the salts and solvates isolated in pure form or when admixed with other materials, for example other isomers and/or polymorphic forms and/or salt forms or any other material.

Solvates, including hydrates, have some variability in the exact molar ratio of their components depending on a variety of conditions understood to a person of skill in the art. For example, a molar ratio of components within a solvate provides a person of skill in the art information as to the general relative quantities of the components of the solvate and in many cases the molar ratio may vary by about plus or minus 20% from a stated range. For example, a molar ratio of 1:1 is understood to include the ratio 1:0.8 as well as 1:1.2 as well as all of the individual ratios in between.

In one embodiment, the present invention comprises dexlansoprazole propylene glycolate monohydrate wherein the ratio of dexlansoprazole to propylene glycol to water is approximately 1:1:1.

In another embodiment, the present invention comprises dexlansoprazole propylene glycolate hydrate wherein the said propylene glycol component is present in approximately equal proportions of (R) absolute configuration and (S) absolute configuration.

In another embodiment, the present invention comprises dexlansoprazole propylene glycolate hydrate wherein the said propylene glycol component is present in predominantly (R) absolute configuration.

In another embodiment, the present invention comprises dexlansoprazole propylene glycolate hydrate wherein the said propylene glycol component is present in predominantly (S) absolute configuration.

In another embodiment, the present invention comprises dexlansoprazole propylene glycolate hydrate wherein the propylene glycol component is present in an (R):(S) ratio of any proportion of (R) absolute configuration of propylene glycol and (S) absolute configuration of propylene glycol provided that the (R):(S) ratio is not approximately 1:1.

In one embodiment, the present invention comprises Form APO-I dexlansoprazole propylene glycolate monohydrate wherein the ratio of dexlansoprazole to propylene glycol to water is approximately 1:1:1.

In another embodiment, the present invention comprises Form APO-I dexlansoprazole propylene glycolate hydrate wherein the said propylene glycol component is present in approximately equal proportions of (R) absolute configuration and (S) absolute configuration.

In another embodiment, the present invention comprises Form APO-I dexlansoprazole propylene glycolate hydrate wherein the said propylene glycol component is present in predominantly (R) absolute configuration.

In another embodiment, the present invention comprises Form APO-I dexlansoprazole propylene glycolate hydrate wherein the said propylene glycol component is present in predominantly (S) absolute configuration.

In another embodiment, the present invention comprises Form APO-I dexlansoprazole propylene glycolate hydrate wherein the propylene glycol component is present in an (R):(S) ratio of any proportion of (R) absolute configuration of propylene glycol and (S) absolute configuration of propylene glycol provided that the (R):(S) ratio is not approximately 1:1.

Figure 6:
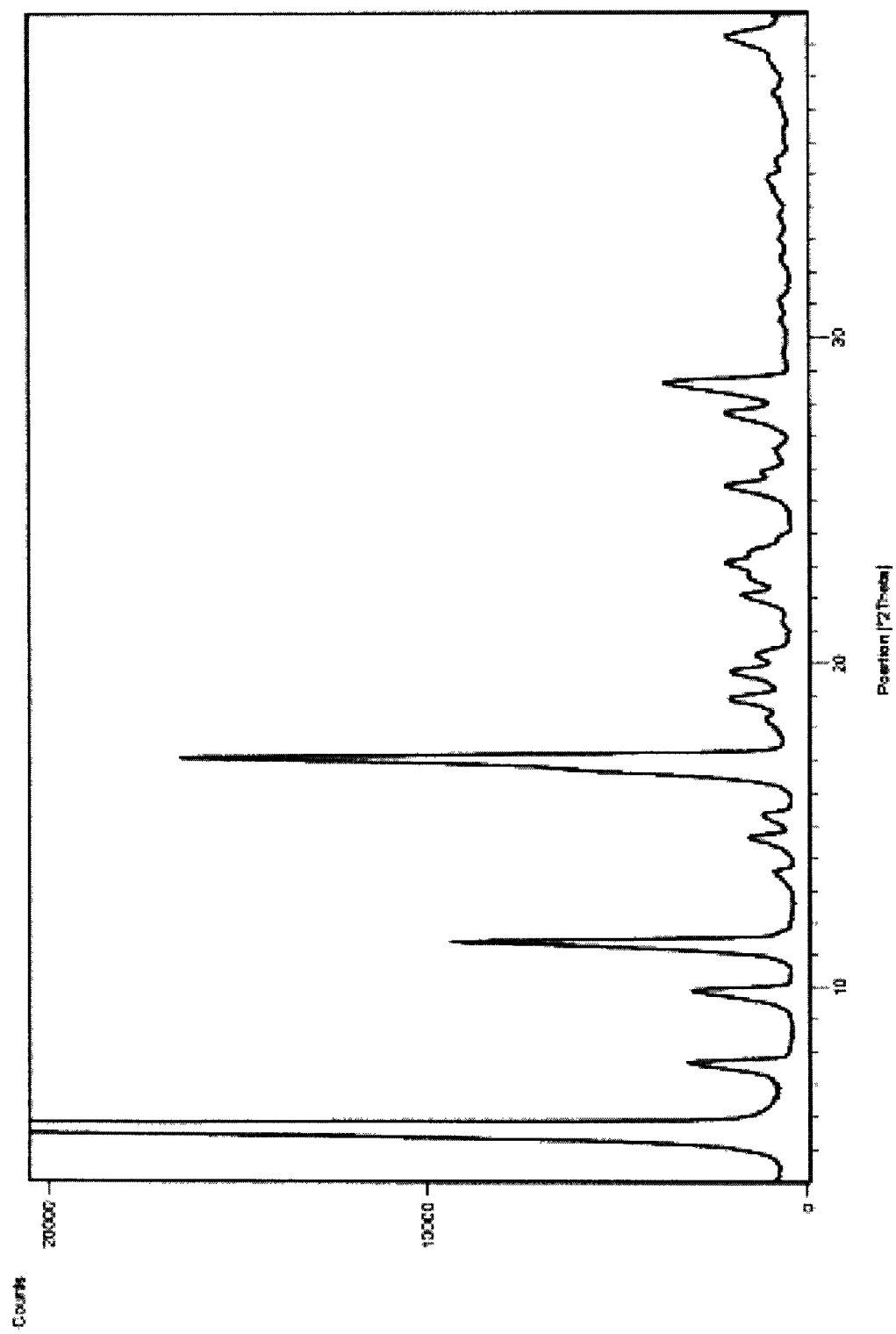
FIG. 6 is a Powder X-Ray Diffraction (PXRD) diffractogram of unground From I dexlansoprazole propylene glycolate hydrate (CuKα).

Illustrative PXRD diffractograms of Form APO-I dexlansoprazole propylene glycolate hydrate acquired according to the conditions given in Example 7 are shown in FIGS. 1 and 6. According to FIG. 1, the Form APO-I dexlansoprazole propylene glycolate hydrate was lightly ground before acquiring the PXRD diffractogram and may have a reflection ("peak") at any one or more of the values expressed in degrees 2θ given in Table 1. According to FIG. 6, the Form APO-I dexlansoprazole propylene glycolate hydrate was not ground before acquiring the PXRD diffractogram and may have a reflection ("peak") at any one or more of the values expressed in degrees 2θ given in Table 1.1. Although values are given in the tables below, the solvate may be defined by the claimed peaks and a particular claim may be limited to one peak only, or several peaks. The Form APO-I dexlansoprazole propylene glycolate hydrate does not have to include all or even many of the peaks listed in Tables 1 and/or 1.1. Some illustrative and non-limiting possible observations regarding relative intensities of the peaks are set out in Table 1 and 1.1.

TABLE 1

Lightly Ground Form APO-I Dexlansoprazole Propylene Glycolate Hydrate

| Peak (degrees 2θ) | Relative Intensity (%) |
|---|---|
| 5.63 | 100.00 |
| 7.60 | 19.90 |
| 9.83 | 18.31 |
| 11.28 | 13.23 |
| 13.47 | 5.44 |
| 14.57 | 4.53 |
| 15.23 | 6.73 |
| 16.97 | 27.06 |
| 18.24 | 22.57 |
| 18.83 | 9.30 |
| 19.66 | 15.01 |
| 20.26 | 22.66 |
| 21.28 | 7.26 |
| 22.59 | 23.35 |
| 23.00 | 11.75 |

TABLE 1-continued

Lightly Ground Form APO-I Dexlansoprazole Propylene Glycolate Hydrate

| Peak (degrees 2θ) | Relative Intensity (%) |
|---|---|
| 25.85 | 17.42 |
| 26.60 | 9.71 |
| 27.63 | 5.88 |
| 28.36 | 10.29 |
| 29.06 | 13.31 |

TABLE 1.1

Unground Form APO-I Dexlansoprazole Propylene Glycolate Hydrate

| Peak (degrees 2θ) | Relative Intensity (%) |
|---|---|
| 5.67 | 100.00 |
| 7.64 | 3.83 |
| 9.88 | 3.79 |
| 11.38 | 12.52 |
| 13.53 | 0.67 |
| 14.66 | 1.56 |
| 15.28 | 1.12 |
| 17.08 | 22.34 |
| 18.22 | 0.82 |
| 18.87 | 2.26 |
| 19.70 | 2.12 |
| 20.27 | 1.32 |
| 21.32 | 0.34 |
| 22.57 | 1.45 |
| 23.08 | 2.23 |
| 25.90 | 1.14 |
| 26.50 | 0.54 |
| 27.64 | 2.03 |
| 28.55 | 4.51 |

Figure 2:
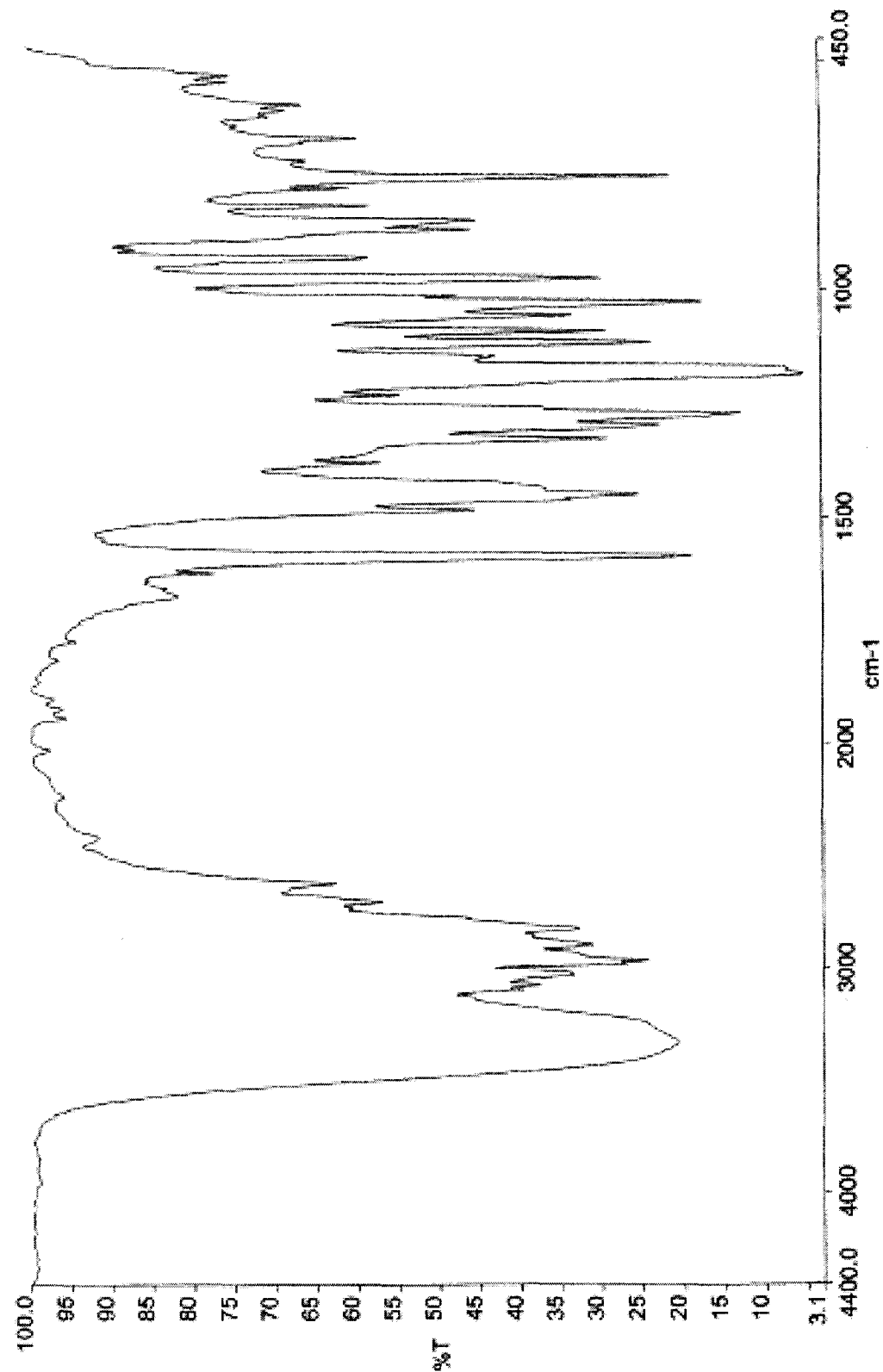
FIG. 2 is a Fourier Transform Infrared (FTIR) spectrum of Form APO-I dexlansoprazole propylene glycolate hydrate (1% KBr).

An illustrative FTIR spectrum of Form APO-I dexlansoprazole propylene glycolate hydrate acquired according to the conditions given in Example 9 is shown in FIG. 2. According to FIG. 2, the Form APO-I dexlansoprazole propylene glycolate hydrate may have an absorption band ("peak") at any one or more of the values expressed in $cm^{-1}$ given in Table 2. Some illustrative and non-limiting possible observations regarding peak intensity (% Transmission) of the peaks are set out in Table 2.

TABLE 2

Form APO-I Dexlansoprazole Propylene Glycolate Hydrate

| Peak ($cm^{-1}$) | Intensity (% Transmission) |
|---|---|
| 3328 | 21 |
| 3070 | 38 |
| 3025 | 33 |
| 2963 | 24 |
| 2893 | 31 |
| 2816 | 33 |
| 2699 | 57 |
| 2616 | 62 |
| 1620 | 77 |
| 1584 | 19 |
| 1478 | 45 |
| 1444 | 25 |
| 1372 | 57 |
| 1320 | 29 |
| 1292 | 23 |
| 1266 | 13 |
| 1224 | 54 |
| 1183 | 5 |

Figure 3:
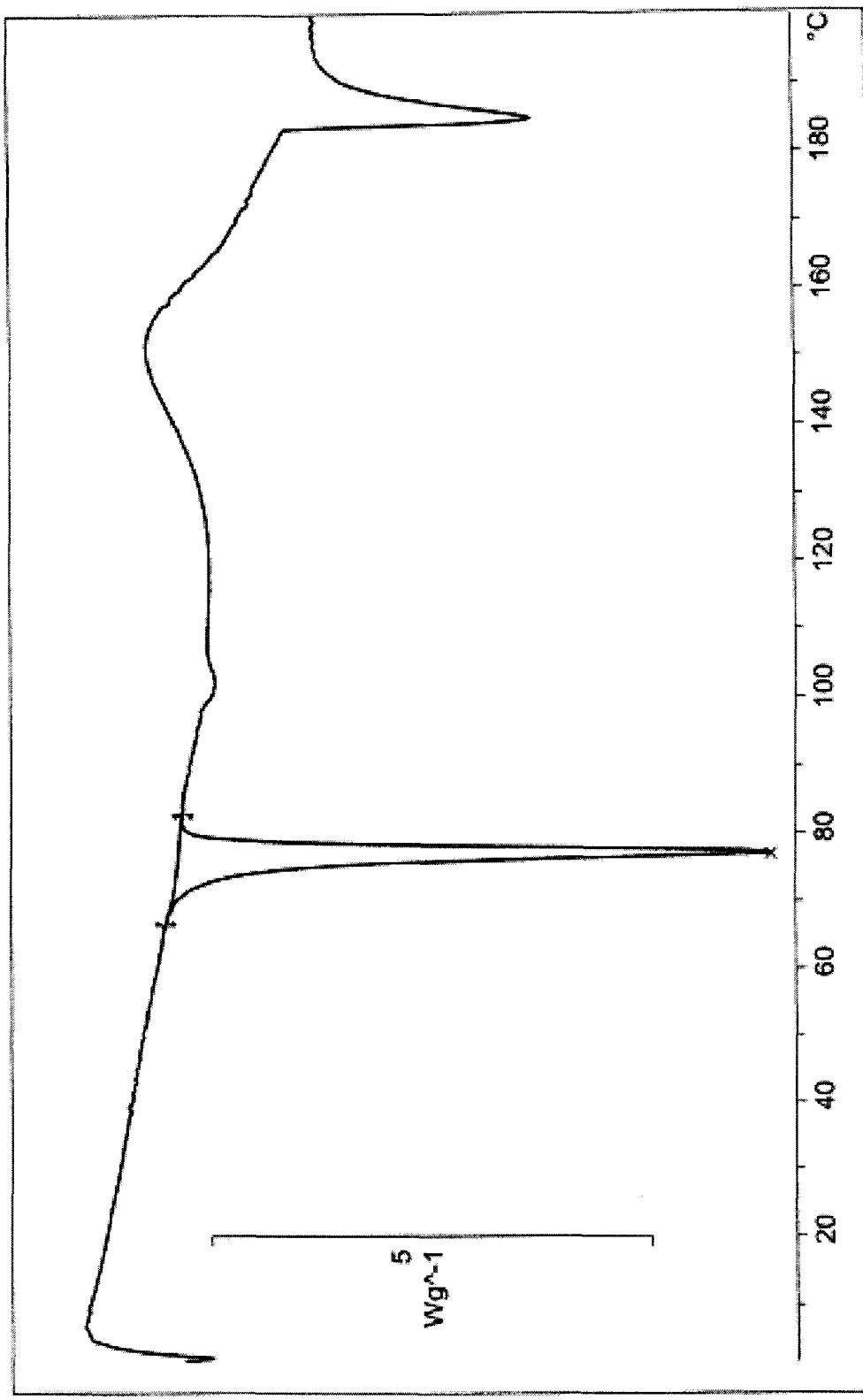
FIG. 3 is a Differential Scanning calorimetry (DSC) thermogram of Form APO-I dexlansoprazole propylene glycolate hydrate.

An illustrative DSC thermogram of Form APO-I dexlansoprazole propylene glycolate hydrate acquired according to the conditions given in Example 8 is shown in FIG. 3. The DSC thermogram shown in FIG. 3 may be illustrative of the type of results obtained when analysing Form APO-I dexlansoprazole propylene glycolate hydrate by DSC. The DSC thermogram may be further characterized by a peak endotherm with an onset temperature of approximately 75° C. and a peak maximum of approximately 77° C.

Figure 9:
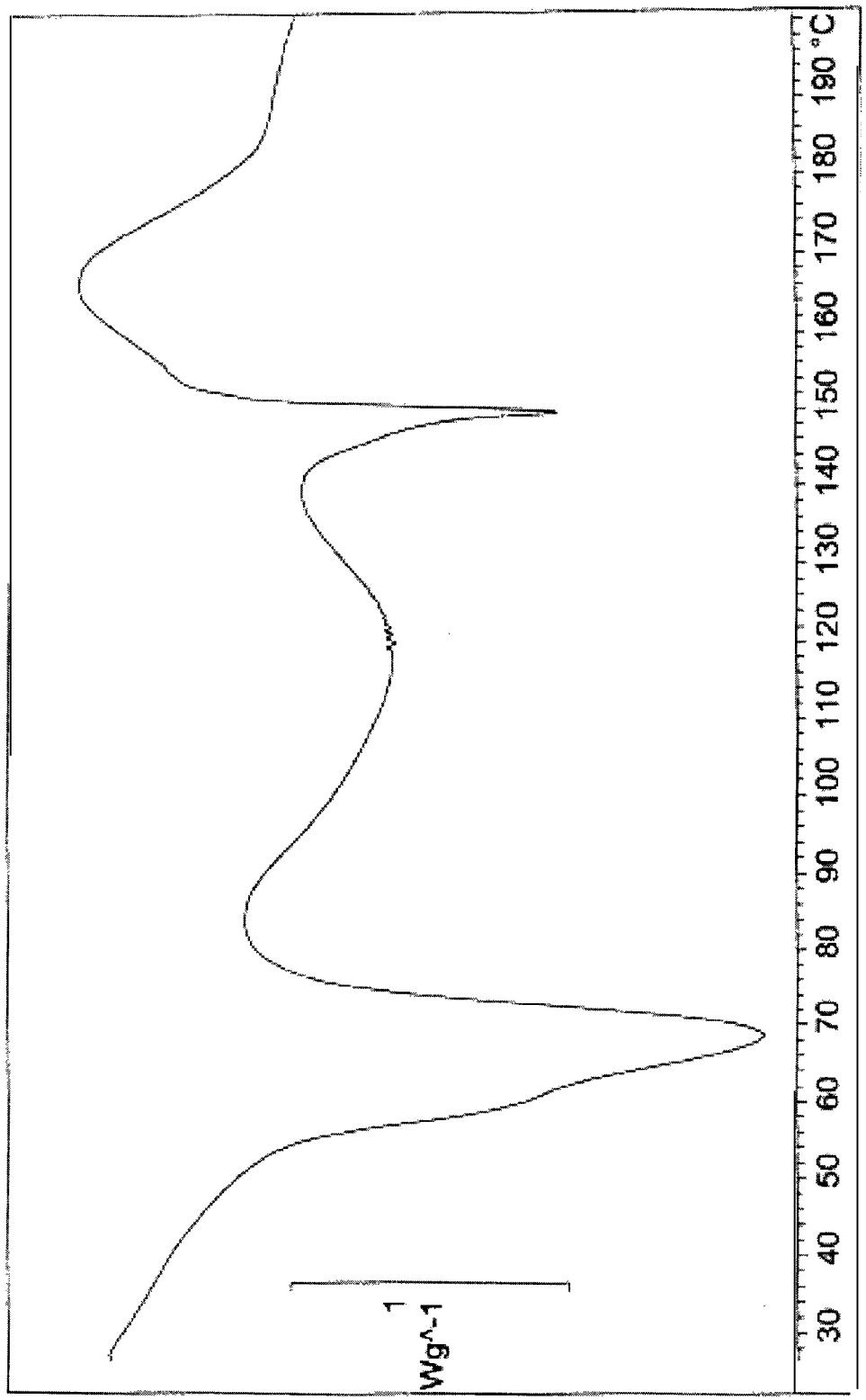
FIG. 9 is a Differential Scanning calorimetry (DSC) thermogram of Form APO-I dexlansoprazole propylene glycol hydrate.

In another illustrative DSC thermogram of dexlansoprazole propylene glycol hydrate acquired according to the conditions given in Example 10 is shown in FIG. 9. The DSC thermogram shown in FIG. 9 may be illustrative of the type of results obtained when analysing dexlansoprazole propylene glycol hydrate by DSC. The DSC thermogram may be further characterized by a peak endotherm with an onset temperature of approximately 53° C. and a peak maximum of approximately 68° C.

In one embodiment, the present invention comprises Form APO-II dexlansoprazole propylene glycolate monohydrate wherein the ratio of dexlansoprazole to propylene glycol to water is approximately 1:1:1.

In another embodiment, the present invention comprises Form APO-II dexlansoprazole propylene glycolate hydrate wherein the said propylene glycol component is present in approximately equal proportions of (R) absolute configuration and (S) absolute configuration.

In another embodiment, the present invention comprises Form APO-II dexlansoprazole propylene glycolate hydrate wherein the said propylene glycol component is present in predominantly (R) absolute configuration.

In another embodiment, the present invention comprises Form APO-II dexlansoprazole propylene glycolate hydrate wherein the said propylene glycol component is present in predominantly (S) absolute configuration.

In another embodiment, the present invention comprises Form APO-II dexlansoprazole propylene glycolate hydrate wherein the propylene glycol component is present in an (R):(S) ratio of any proportion of (R) absolute configuration of propylene glycol and (S) absolute configuration of propylene glycol provided that the (R):(S) ratio is not approximately 1:1.

Figure 7:
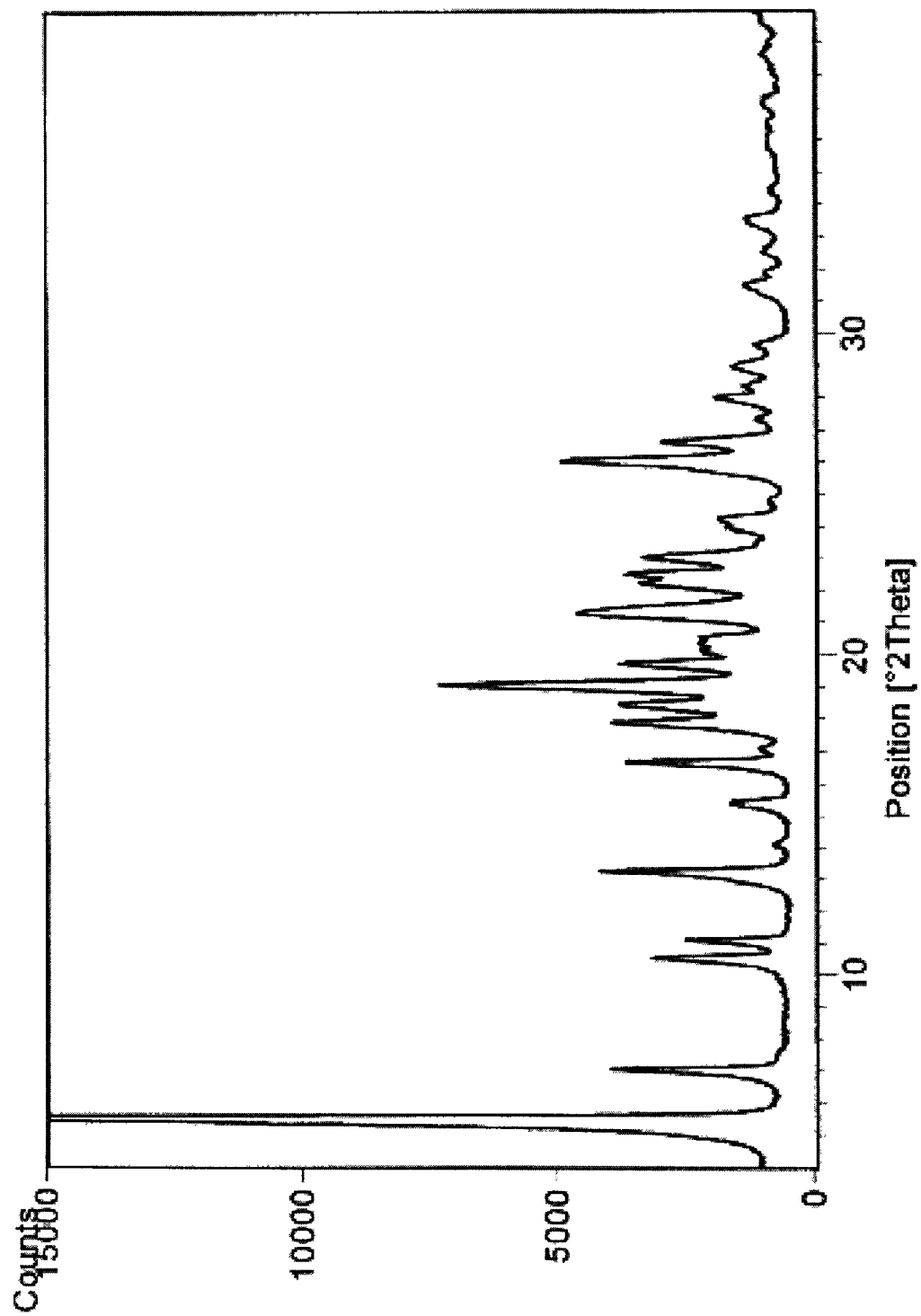
FIG. 7 is a Powder X-Ray Diffraction (PXRD) diffractogram of Form APO-II dexlansoprazole propylene glycolate hydrate.

An illustrative PXRD diffractogram of Form APO-II dexlansoprazole propylene glycolate hydrate acquired according to the conditions given in Example 7 is shown in FIG. 7. According to FIG. 7, the Form APO-II dexlansoprazole propylene glycolate hydrate was lightly ground before acquiring the PXRD diffractogram and may have a reflection ("peak") at any one or more of the values expressed in degrees 2θ given in Table 3. Although values are given in the tables below, the solvate may be defined by the claimed peaks and a particular claim may be limited to one peak only, or several peaks. The Form APO-II dexlansoprazole propylene glycolate hydrate does not have to include all or even many of the peaks listed in Table 3. Some illustrative and non-limiting possible observations regarding relative intensities of the peaks are set out in Table 3.

TABLE 3

Lightly Ground Form APO-II Dexlansoprazole Propylene Glycolate Hydrate

| Peak (degrees 2θ) | Relative Intensity (%) |
|---|---|
| 5.51 | 100 |
| 7.02 | 11.75 |
| 10.50 | 8.92 |
| 11.07 | 7.28 |
| 13.23 | 12.28 |

TABLE 3-continued

Lightly Ground Form APO-II Dexlansoprazole Propylene Glycolate Hydrate

| Peak (degrees 2θ) | Relative Intensity (%) |
|---|---|
| 15.44 | 3.96 |
| 16.65 | 11.50 |
| 17.86 | 12.69 |
| 18.43 | 8.63 |
| 19.04 | 25.91 |
| 19.70 | 11.91 |
| 20.51 | 6.18 |
| 21.26 | 14.53 |
| 22.20 | 10.12 |
| 22.51 | 11.67 |
| 23.02 | 9.87 |
| 23.94 | 4.07 |
| 26.01 | 15.72 |
| 26.62 | 9.14 |
| 27.96 | 4.54 |

Figure 8:
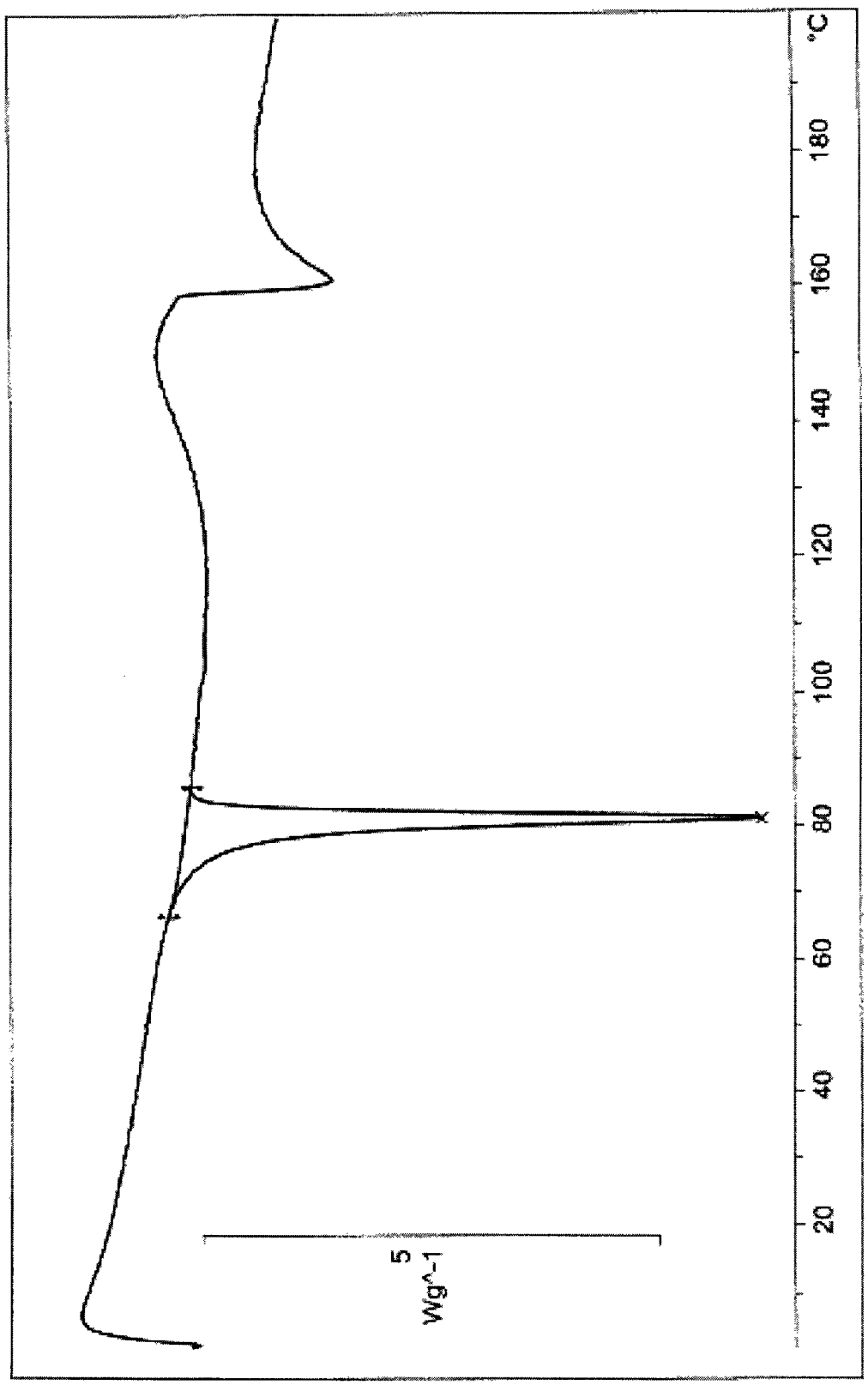
FIG. 8 is a Differential Scanning calorimetry (DSC) thermogram of Form APO-II dexlansoprazole propylene glycolate hydrate.

An illustrative DSC thermogram of Form APO-II dexlansoprazole propylene glycolate hydrate acquired according to the conditions given in Example 8 is shown in FIG. 8. The DSC thermogram shown in FIG. 8 may be illustrative of the type of results obtained when analysing Form APO-II dexlansoprazole propylene glycolate hydrate by DSC. The DSC thermogram may be further characterized by a peak endotherm with an onset temperature of approximately 78° C. and a peak maximum of approximately 81° C.

In one embodiment, the present invention comprises crystalline dexlansoprazole isopropylammonium salt wherein the molar ratio of dexlansoprazole to isopropyl amine is approximately 1:1.

Figure 4:
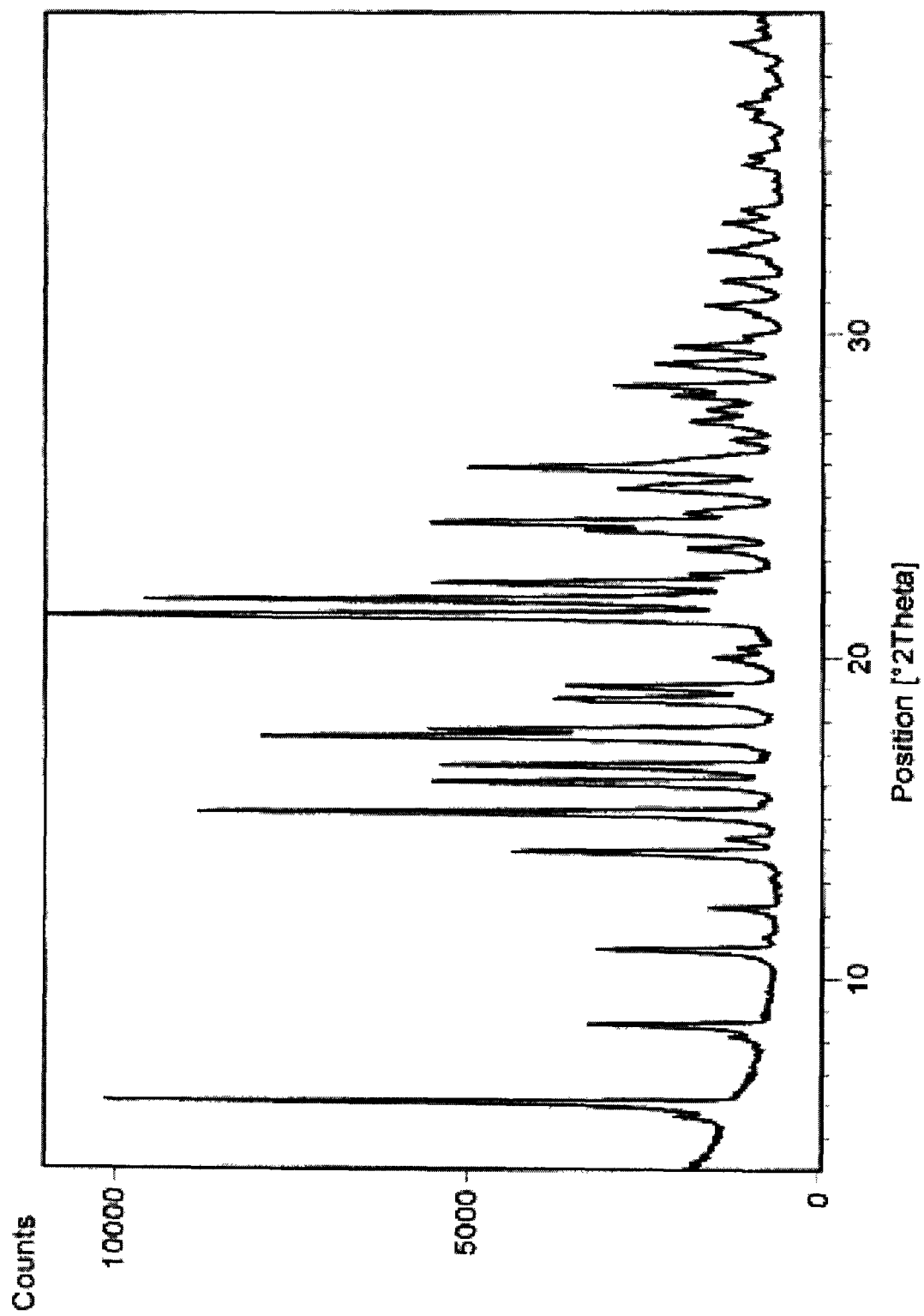
FIG. 4 is a Powder X-Ray Diffraction (PXRD) diffractogram of dexlansoprazole isopropylammonium salt (CuKα).

An illustrative PXRD diffractogram of crystalline dexlansoprazole isopropylammonium salt acquired according to the conditions given in Example 7 is shown in FIG. 4. According to FIG. 4, the dexlansoprazole isopropylammonium salt may have a reflection ("peak") at any one or more of the values expressed in degrees 2θ given in Table 4. Although values are given in the table below, the salt is defined by the claimed peaks and a particular claim may be limited to one peak only, or several peaks. The dexlansoprazole isopropylammonium salt does not have to include all or even many of the peaks listed in Table 4. Some illustrative and non-limiting possible observations regarding relative intensities of the peaks are set out in Table 4.

TABLE 4

Dexlansoprazole Isopropylammonium Salt

| Peak (degrees 2θ) | Relative Intensity (%) |
|---|---|
| 6.10 | 80.29 |
| 8.54 | 23.62 |
| 10.89 | 23.81 |
| 12.21 | 8.65 |
| 13.92 | 35.70 |
| 14.35 | 7.28 |
| 15.17 | 73.67 |
| 16.09 | 46.46 |
| 16.62 | 44.86 |
| 17.52 | 65.42 |
| 17.75 | 48.97 |
| 18.67 | 29.25 |
| 19.07 | 28.89 |
| 19.94 | 7.25 |
| 20.28 | 5.51 |
| 21.29 | 100 |
| 21.78 | 84.13 |
| 22.28 | 45.53 |

TABLE 4-continued

Dexlansoprazole Isopropylammonium Salt

| Peak (degrees 2θ) | Relative Intensity (%) |
|---|---|
| 22.57 | 14.61 |
| 23.35 | 11.49 |
| 23.92 | 25.17 |
| 24.18 | 49.16 |
| 24.50 | 12.60 |
| 25.23 | 20.60 |
| 25.87 | 40.93 |
| 26.71 | 5.67 |
| 27.30 | 11.16 |
| 27.69 | 9.67 |
| 28.11 | 13.32 |
| 28.40 | 22.45 |
| 29.09 | 16.73 |
| 29.63 | 13.19 |
| 30.87 | 9.33 |
| 31.62 | 7.26 |
| 32.58 | 8.44 |
| 33.40 | 6.43 |

In one embodiment, the present invention comprises MTBE solvate of dexlansoprazole t-butylammonium salt wherein the molar ratio of dexlansoprazole to t-butyl amine to MTBE is approximately 3:3:2.

Figure 5:
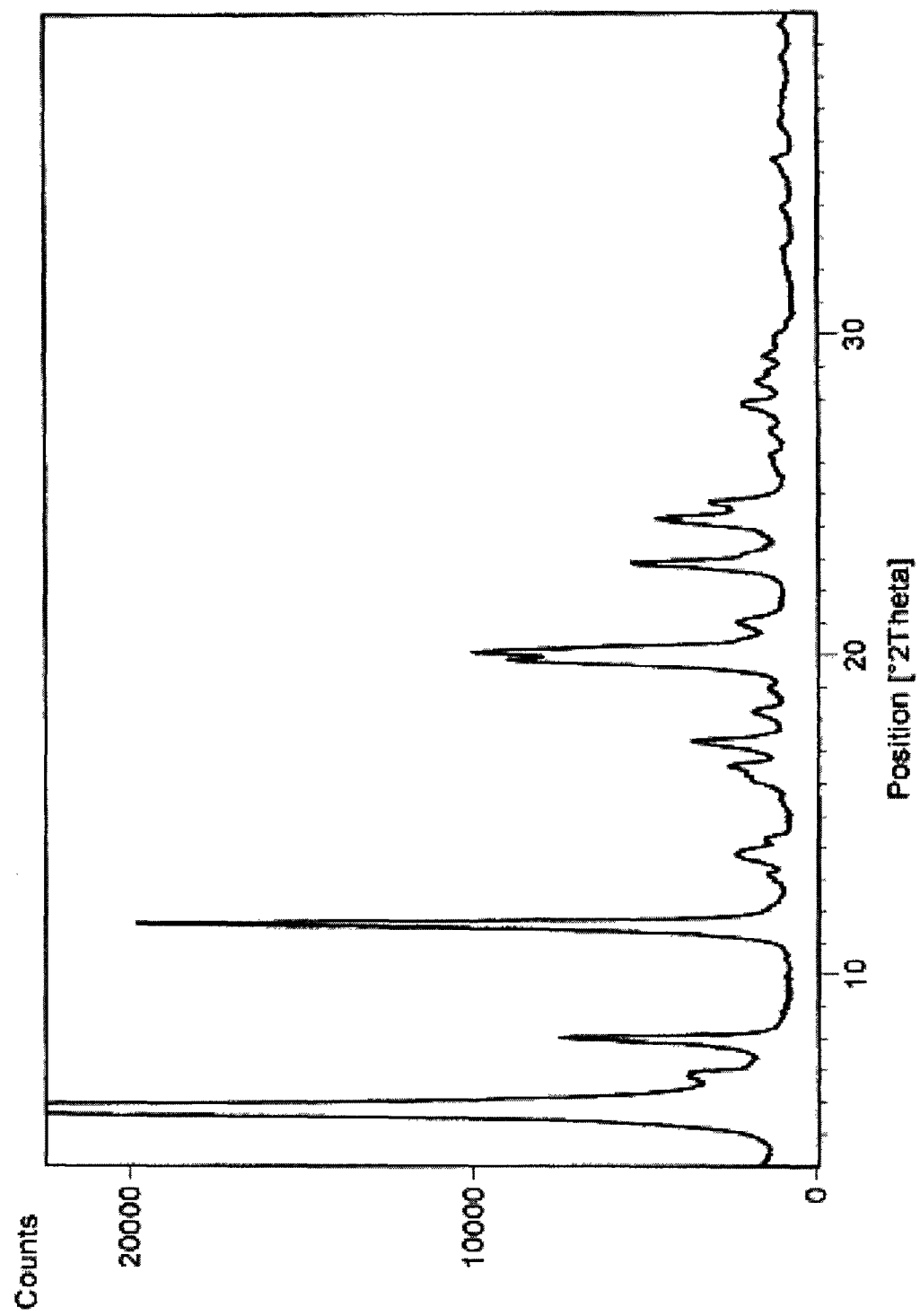
FIG. 5 is a Powder X-Ray Diffraction (PXRD) diffractogram of the MTBE solvate of dexlansoprazole t-butylammonium salt (CuKα).

An illustrative PXRD diffractogram of MTBE solvate of dexlansoprazole t-butylammonium salt acquired according to the conditions given in Example 7 is shown in FIG. 5. According to FIG. 5, the MTBE solvate of dexlansoprazole t-butylammonium salt may have a reflection ("peak") at any one or more of the values expressed in degrees 2θ given in Table 5.

Although values are given in the table below, the salt is defined by the claimed peaks and a particular claim may be limited to one peak only, or several peaks. The dexlansoprazole t-butyl amine salt does not have to include all or even many of the peaks listed in Table 5. Some illustrative and non-limiting possible observations regarding relative intensities of the peaks are set out in Table 5.

TABLE 5

MTBE solvate of Dexlansoprazole t-butylammonium salt

| Peak (degrees 2θ) | Relative Intensity (%) |
|---|---|
| 5.80 | 100.00 |
| 6.80 | 3.28 |
| 7.98 | 8.22 |
| 11.60 | 23.50 |
| 13.77 | 2.04 |
| 16.56 | 2.21 |
| 17.28 | 3.55 |
| 18.23 | 1.35 |
| 19.82 | 9.98 |
| 20.10 | 11.63 |
| 20.16 | 10.64 |
| 20.98 | 1.98 |
| 22.83 | 5.45 |
| 24.22 | 4.91 |
| 24.73 | 3.20 |
| 27.79 | 1.88 |

In an embodiment, the present invention comprises a process for preparation of dexlansoprazole propylene glycolate hydrate comprising:
 a. combining dexlansoprazole with propylene glycol and water in the presence of a first organic solvent to form a mixture;
 b. heating the mixture to form a solution;
 c. promoting crystal growth thereby forming crystals; and
 d. collecting crystals.

Dexlansoprazole used in the process for the preparation of dexlansoprazole propylene glycolate hydrate described herein may be any form of dexlansoprazole, including any polymorphic form, such as amorphous, anhydrate and hydrate forms. The dexlansoprazole may be provided as a solution from a previous step. In an embodiment, the enantiomeric excess of the sample of dexlansoprazole to be applied to the process of the present invention is not less than about 80% ee.

The first organic solvent is free of any particular limitation as long as the process proceeds. Examples of the first organic solvent include aromatic hydrocarbons (eg. benzene, toluene and xylene, etc.), ethers (eg. methyl tert-butyl ether (MTBE), diethyl ether, tetrahydrofuran and diisopropyl ether, etc.), esters (eg. ethyl acetate and isopropyl acetate, etc.), ketones (eg. acetone, methylisobutylketone, etc.), alcohols (eg. ethanol, isopropanol and butyl alcohol, etc.), halogenated hydrocarbons (eg. dichloromethane, chloroform, etc.) and mixtures thereof. Often the first organic solvent is MTBE, toluene or ethyl acetate.

The amounts, relative to dexlansoprazole, of propylene glycol, first organic solvent and water are from about 0.2 volumes to about 4 volumes, from about 4 volumes to about 40 volumes, and from about 0.05 volumes to about 2 volumes, respectively.

The mixture may be heated to a temperature sufficient to obtain dissolution. The mixture may be heated to a temperature of between about 35° C. to about 100° C. Often, the mixture is heated to a temperature of between about 40° C. to about 60° C.

Crystal growth may be promoted by cooling the solution. The solution may be cooled to a temperature of between about −5° C. to about 30° C. Often, the solution is cooled to a temperature between about 10° C. to about 25° C.

The crystals may be collected by filtration and optionally washed with the first organic solvent to remove residual propylene glycol. Drying, if desired may also be carried out. Appropriate drying conditions should be chosen to avoid melting and/or desolvation of the dexlansoprazole propylene glycolate hydrate. For example, extreme heat should be avoided during drying conditions. Illustrative drying conditions are in a vacuum oven at about 20 mmHg vacuum or less at a temperature of between about 20° C. to about 30° C.

In an embodiment, the present invention comprises crystalline dexlansoprazole isopropylammonium salt wherein the molar ratio of dexlansoprazole to isopropyl amine is approximately 1:1. The dexlansoprazole isopropyl ammonium salt may be prepared from any form of dexlansoprazole, including any polymorphic form, such as amorphous, anhydrate and hydrate forms. The isopropylammonium salt may be prepared by contacting dexlansoprazole with isopropyl amine under a variety of conditions. For example, dexlansoprazole isopropyl amine salt may be formed by combining dexlansoprazole with isopropyl amine in a second organic solvent in the presence or absence of water followed by optional heating to obtain a mixture that is either heterogenous or homogenous. The amount of isopropyl amine with respect to dexlansoprazole may be from about 0.25 volumes to about 5 volumes. Examples of the second organic solvent include aromatic hydrocarbons (eg. benzene, toluene and xylene, etc.), ethers (eg. methyl tert-butyl ether (MTBE), diethyl ether, tetrahydrofuran and diisopropyl ether, etc.), esters (eg. ethyl acetate and isopropyl acetate, etc.), ketones (eg. acetone, methylisobutylketone, etc.), alcohols (eg. ethanol, isopropanol and butyl alcohol, etc.), halogenated hydrocarbons (eg. dichloromethane, chloroform, etc.) and mixtures thereof. Often the second organic solvent is MTBE, toluene or ethyl acetate. The amount of the second organic solvent with respect to dexlansoprazole may be from about 5 volumes to about 40 volumes. If necessary, the mixture may be cooled to promote crystal growth. The mixture may be cooled to a temperature of between about −5° C. to about 30° C., often between about 10° C. and 25° C. The crystals of dexlansoprazole isopropyl amine may be collected by filtration and dried, if desired. The drying may be done, for example, in a vacuum oven at 20 mmHg vacuum or less at a temperature between about 20° C. to about 50° C.

In one embodiment, the present invention comprises MTBE solvate of dexlansoprazole t-butylammonium salt wherein the molar ratio of dexlansoprazole to t-butyl amine to MTBE is approximately 3:3:2. The MTBE solvate of dexlansoprazole t-butylammonium salt may be prepared from any form of dexlansoprazole, including any polymorphic form, such as amorphous, anhydrate and hydrate forms. The MTBE solvate of the t-butyl ammonium salt may be prepared by contacting dexlansoprazole with t-butyl amine and MTBE under a variety of conditions. For example, the MTBE solvate of the t-butylammonium salt may be formed by combining dexlansoprazole with t-butyl amine in a second organic solvent in the presence or absence of water followed by optional heating to obtain a mixture that is either heterogenous or homogenous. The amount of t-butyl amine with respect to dexlansoprazole may be from about 0.3 volumes to about 5 volumes. The amount of MTBE with respect to dexlansoprazole may be from about 5 volumes to about 40 volumes. If necessary, the mixture may be cooled to promote crystal growth. The mixture may be cooled to a temperature of between about −5° C. to about 30° C., often between about 10° C. and 25° C. The crystals of MTBE solvate of dexlansoprazole t-butyl ammonium salt may be collected by filtration and dried, if desired. The drying may be done, for example, in a vacuum oven at 20 mmHg vacuum or less at a temperature between about 20° C. to about 30° C.

EXAMPLES

The following examples are illustrative of some of the embodiments of the invention described herein. These examples should not be considered to limit the spirit or scope of the invention in any way.

Example 1

Preparation of Form APO-I Dexlansoprazole Propylene Glycolate Hydrate

Dexlansoprazole (2 g) in amorphous form was dissolved in racemic propylene glycol (0.3 mL) and MTBE (20 mL) followed by the addition of water (0.15 mL). After stirring at room temperature for several minutes, the resulting suspension was heated to about 50° C. to obtain dissolution. A suspension was formed after cooling to room temperature. The suspension was filtered, washed with MTBE/hexanes (100 mL, 1:1, v/v) and dried in vacuo at 20-25° C. to provide Form APO-I dexlansoprazole propylene glycolate hydrate (1.2 g). Water content: 4%; molar ratio of dexlansoprazole to propylene glycol is 1:1 by $^1$H NMR.

Example 2

Preparation of Form APO-II Dexlansoprazole Propylene Glycolate Hydrate

Form APO-I dexlansoprazole propylene glycolate hydrate (6.81 g) prepared as in Example 1 was suspended in MTBE (100 mL) in a round bottom flask, and the suspension was stirred at room temperature under a nitrogen atmosphere. Racemic propylene glycol (3.24 mL) was added to the mixture which was stirred while heating in a 40° C. oil bath. Once the reaction mixture became a clear solution, the heating was stopped and the solution was stirred while cooling to room temperature. A thick suspension with white precipitate soon formed, which was then cooled to 0-5° C. with stirring. The suspension was filtered and the filter cake was washed with MTBE (2×25 mL). The filter cake was suspended in a 1:1 mixture of MTBE:heptanes (100 mL) and stirred at room temperature for 20 minutes. The suspension was filtered and the filter cake was washed with a 1:1 mixture of MTBE: heptanes (3×25 mL) and dried in vacuo at 20-25° C. to provide Form APO-II dexlansoprazole propylene glycolate hydrate (5.11 g). Water content: 4%; molar ratio of dexlansoprazole to propylene glycol is 1:1 by $^1$H-NMR.

Example 3

Preparation of Form APO-I Dexlansoprazole Propylene Glycolate Hydrate

Dexlansoprazole (13.1 g) was dissolved in MTBE (200 mL) in a round bottom flask and stirred at room temperature giving a clear solution. (S)-Propylene glycol (3.91 mL) was added to the mixture, followed by water (1.92 mL) and the mixture was stirred at room temperature. A clear solution was obtained. After approximately 15 minutes a thick suspension formed. The suspension was heated to an internal temperature of approximately 35 to 40° C. with stirring. When the internal temperature of the mixture was 36 to 37° C. the mixture was a clear solution with a small amount of undissolved suspended solids. The mixture was filtered without cooling, and the filter cake was washed with MTBE (2×20 mL). The combined mother liquor was stirred while cooling to room temperature. Upon cooling to room temperature a suspension had formed; heptanes (100 mL) was added and the suspension was stirred at room temperature for 3 hours. The suspension was filtered and the cake was washed with a 1:1 mixture of MTBE:heptanes (50 mL). The damp filter cake was suspended in a 1:1 mixture of MTBE:heptanes (250 mL) and stirred at room temperature for 20 minutes. The suspension was filtered and the filter cake was washed with a 1:1 mixture of MTBE:heptanes (3×25 mL) and dried in vacuo at 20-25° C. to provide Form APO-I dexlansoprazole (S)-propylene glycolate hydrate (10.81 g). Water content: 4%; molar ratio of dexlansoprazole to propylene glycol is 1:1 by $^1$H-NMR.

Example 4

Preparation of Form APO-II Dexlansoprazole Propylene Glycolate Hydrate

Dexlansoprazole (15.0 g) was dissolved in MTBE (150 mL) in a round bottom flask and stirred at room temperature; some undissolved solids remained. (R)-Propylene glycol (4.47 mL) was added to the mixture, followed by water (2.19 mL) and the mixture was stirred at room temperature. A clear solution was obtained, which quickly turned into a thick suspension. The suspension was heated to an internal temperature of approximately 40° C. The mixture remained a suspension at 40° C.; more MTBE (75 mL) was added and heating was continued. Once the internal temperature reached 50° C., the reaction mixture was nearly a clear solution, with some undissolved solids. Heating was stopped and the reaction mixture allowed to cool slowly to room temperature with stirring. Upon cooling to room temperature, a thick suspension with white precipitate had formed. The suspension was filtered and the cake was washed with a 1:1 mixture of MTBE: heptanes (2×50 mL). The damp filter cake was suspended in a 1:1 mixture of MTBE:heptanes (250 mL) and stirred at room temperature for 20 minutes. The suspension was filtered and the filter cake was washed with a 1:1 mixture of MTBE: heptanes (3×25 mL) and dried in vacuo at 20-25° C. to provide Form APO-II dexlansoprazole (R)-propylene glycolate hydrate (15.36 g). Water content: 4%; molar ratio of dexlansoprazole to propylene glycol is 1:1 by $^1$H-NMR.

Example 5

Preparation of Dexlansoprazole Isopropylammonium Salt

Dexlansoprazole (2 g) in amorphous form was dissolved in MTBE (50 mL) followed by the addition of isopropyl amine (3 mL). After stirring at room temperature for 30 minutes, the resulting suspension was filtered, washed with MTBE (10 mL) and dried in vacuo at 20-25° C. to provide dexlansoprazole isopropylammonium salt (2.1 g). Molar ratio of dexlansoprazole to isopropyl amine is 1:1 by $^1$H NMR.

Example 6

Preparation of Dexlansoprazole Tert-Butylammonium MTBE Solvate

Dexlansoprazole (1 g) in amorphous form was dissolved in MTBE (50 mL) followed by the addition of tert-butyl amine (0.6 mL). After stirring at room temperature for several minutes, the resulting suspension was heated to gentle reflux to obtain dissolution. A suspension was formed after cooling to room temperature. The suspension was filtered, washed with MTBE (10 mL) and dried in vacuo at 20-25° C. to provide dexlansoprazole tert-butylammonium MTBE solvate (1.1 g). The molar ratio of dexlansoprazole to tert-butyl amine to MTBE is approximately 3:3:2 respectively by $^1$H NMR.

Example 7

Powder X-Ray Diffraction (PXRD) Analysis

The PXRD diffractograms of Form APO-I dexlansoprazole propylene glycolate hydrate (as prepared in Example 1), Form APO-II dexlansoprazole propylene glycolate hydrate (as prepared in Example 2), dexlansoprazole isopropylammonium salt (as prepared in Example 5) and MTBE solvate of dexlansoprazole t-butylammonium salt (as prepared in Example 6) are given in FIGS. 1, 7, 4 and 5, respectively. An additional PXRD diffractogram of Form APO-I dexlansoprazole propylene glycolate hydrate (as prepared in Example 1) is provided in FIG. 6. The difference between the sample used to generate the PXRD diffractogram of FIGS. 1 and 6 is that the sample was lightly ground prior to acquiring the PXRD diffractogram. It is possible to lightly grind a sample in a mortar and pestle prior to PXRD analysis to reduce preferred orientation effects. Excessive grinding may significantly alter the diffraction diffractogram or cause an increase in the amorphous content of the sample and was avoided. The data were acquired on a PANalytical X'Pert Pro MPD diffractometer with fixed divergence slits and an X'Celerator RTMS detector. The diffractometer was configured in Bragg-Brentano geometry; data was collected over a 2 theta range of 4-40 using CuKα radiation at a power of 40 mA and 45 kV. CuKβ radiation was removed using a divergent beam nickel filter. A step size of 0.017 degrees was used. For unground Form APO-I dexlansoprazole propylene glycolate hydrate (see FIG. 6), Form APO-II dexlansoprazole propylene glycolate hydrate (see FIG. 7), dexlansoprazole isopropylammonium salt (see FIG. 4), and the MTBE solvate of dexlansoprazole tert-butylammonium salt (see FIG. 5), a step time of 20.7 seconds were used. For ground Form APO-I dexlansoprazole propylene glycolate hydrate (see FIG. 1), a step time of 80 seconds was used. Samples were rotated at 1 Hz to reduce preferred orientation effects. The samples were prepared by the back-loading technique.

Example 8

Differential Scanning Calorimetry (DSC) Analysis

DSC thermograms of Form APO-I dexlansoprazole propylene glycolate hydrate (as prepared in Example 1) and Form APO-II dexlansoprazole propylene glycolate hydrate (as prepared in Example 2) are given in FIGS. 3 and 8. The DSC thermograms were collected on a Mettler-Toledo 821e instrument. Samples (1-5 mg) were weighed into a 40 μL aluminum pan and were crimped closed with an aluminum lid. The samples were analyzed under a flow of nitrogen (ca. 55 mL/min) at a scan rate of 10° C./minute.

Example 9

Fourier Transform Infrared (FTIR) Analysis

The FTIR spectrum of Form APO-I dexlansoprazole propylene glycolate hydrate (as prepared in Example 1) is given in FIG. 2. The FTIR spectrum was collected at 4 cm$^{-1}$ resolution using a Perkin Elmer Paragon 1100 single beam FTIR instrument. The samples were intimately mixed in an approximately 1:100 ratio (w/w) with potassium bromide using an agate mortar and pestle to a fine consistency; the mixture was compressed in a pellet die at a pressure of 4-6 tonnes for a period of time between 2 and 5 minutes. The resulting disk was scanned 32 times versus a background collected on a nitrogen-enriched atmosphere. Data was baseline corrected and normalized.

Example 10

Differential Scanning Calorimetry (DSC) Analysis

A DSC thermogram of Form APO-I dexlansoprazole propylene glycolate hydrate (as prepared in Example 1) is given in FIG. 9. The DSC thermogram was collected on a Mettler-Toledo 821e instrument. Samples (1-5 mg) were weighed into a 40 μL aluminum pan and were crimped closed with an aluminum lid in which a pinhole had been pierced of between 0.5 and 1.0 mm in diameter. The samples were analyzed under a flow of nitrogen (ca. 55 mL/min) at a scan rate of 10° C./minute.

Although various embodiments of the invention are disclosed herein, many adaptations and modifications may be made within the scope of the invention in accordance with the common general knowledge of those skilled in this art. Such modifications include the substitution of known equivalents for any aspect of the invention in order to achieve the same result in substantially the same way. Numeric ranges are inclusive of the numbers defining the range. The word "comprising" is used herein as an open-ended term, substantially equivalent to the phrase "including, but not limited to", and the word "comprises" has a corresponding meaning. As used herein, the singular forms "a", "an" and "the" include plural referents unless the context clearly dictates otherwise. Thus, for example, reference to "a thing" includes more than one such thing. Citation of references herein is not an admission that such references are prior art to the present invention. Any priority document(s) are incorporated herein by reference as if each individual priority document were specifically and individually indicated to be incorporated by reference herein and as though fully set forth herein. The invention includes all embodiments and variations substantially as hereinbefore described and with reference to the examples and drawings.

What is claimed is:

1. A Form APO-I dexlansoprazole propylene glycolate hydrate having a Powder X-Ray Diffraction (PXRD) diffractogram comprising peaks, in terms of degrees 2θ, at approximately 5.6, 7.6, 9.8, 11.3, 17.0, 18.2 and 28.4.

2. The Form APO-I dexlansoprazole propylene glycolate hydrate of claim 1 having a PXRD diffractogram further comprising peaks, in terms of degrees 2θ, at approximately 19.7, 20.3, 22.6, and 27.6.

3. The Form APO-I dexlansoprazole propylene glycolate hydrate of claim 1 having a PXRD diffractogram substantially similar to the PXRD diffractogram as depicted in FIG. 1.

4. The Form APO-I dexlansoprazole propylene glycolate hydrate of claim 1 having a PXRD diffractogram as depicted in FIG. 1.

5. The Form APO-I dexlansoprazole propylene glycolate hydrate of claim 1 having a PXRD diffractogram substantially similar to the PXRD diffractogram as depicted in FIG. 6.

6. The Form APO-I dexlansoprazole propylene glycolate hydrate of claim 1 having a PXRD diffractogram as depicted in FIG. 6.

7. The Form APO-I dexlansoprazole propylene glycolate hydrate of claim 1 having a 1% KBr Fourier Transform Infrared (FTIR) spectrum comprising peaks, in terms of cm$^{-1}$, at approximately 3328, 3025, 2963, 2893, 2816, 1620, 1320 and 1292.

8. The Form APO-I dexlansoprazole propylene glycolate hydrate of claim 1 having a 1% KBr FTIR spectrum comprising peaks, in terms of cm$^{-1}$, at approximately 3328, 3025, 2963, 2893, 2816, 1620, 1584, 1478, 1444, 1320, 1292, and 1266.

9. The Form APO-I dexlansoprazole propylene glycolate hydrate of claim 1 having a FTIR spectrum substantially similar to the FTIR spectrum as depicted in FIG. 2.

10. The Form APO-I dexlansoprazole propylene glycolate hydrate of claim 1 having a FTIR spectrum as depicted in FIG. 2.

11. The Form APO-I dexlansoprazole propylene glycolate hydrate of claim 1 having a Differential Scanning calorimetry (DSC) thermogram comprising an endothermic peak with a peak onset temperature of approximately 75° C. and a peak maximum of approximately 77° C.

12. The Form APO-I dexlansoprazole propylene glycolate hydrate of claim 1 having a DSC thermogram substantially similar to the DSC thermogram as depicted in FIG. 3.

13. The Form APO-I dexlansoprazole propylene glycolate hydrate of claim 1 having a DSC thermogram as depicted in FIG. 3.

14. The Form APO-I dexlansoprazole propylene glycolate hydrate of claim 1 having a DSC thermogram comprising an endothermic peak with a peak onset temperature of approximately 53° C. and a peak maximum of approximately 68° C.

15. The Form APO-I dexlansoprazole propylene glycolate hydrate of claim 1 having a DSC thermogram substantially similar to the DSC thermogram as depicted in FIG. 9.

16. The Form APO-I dexlansoprazole propylene glycolate hydrate of claim 1 having a DSC thermogram as depicted in FIG. 9.

* * * * *